United States Patent [19]

Giorgi et al.

[11] Patent Number: 4,879,311

[45] Date of Patent: Nov. 7, 1989

[54] DERIVATIVES OF BENZOYLOXYACETIC ACID, AND PREPARATION AND FORMULATIONS THEREOF FOR THERAPEUTIC USE

[75] Inventors: Raffaello Giorgi; Marisa Conti; Giorgio Pifferi, all of Milan, Italy

[73] Assignee: Inverni della Beffa S.p.A., Via Ripamonti, Italy

[21] Appl. No.: 222,552

[22] Filed: Jul. 21, 1988

[30] Foreign Application Priority Data

Jul. 29, 1987 [GB] United Kingdom ................. 8717997

[51] Int. Cl.$^4$ ................... A61K 31/24; C07C 101/447
[52] U.S. Cl. ........................................ 514/533; 560/47
[58] Field of Search ............................ 560/47; 514/533

[56] References Cited

U.S. PATENT DOCUMENTS 4,388,473 6/1983 Richter et al. .......................... 560/47
4,548,952 10/1985 Casas ..................................... 560/47

FOREIGN PATENT DOCUMENTS 733136 4/1966 Canada ................................... 560/47
651821 10/1985 Switzerland .......................... 560/47
1199386 7/1970 United Kingdom .................. 560/47

Primary Examiner—Bruce Gray
Attorney, Agent, or Firm—Kirschstein, Ottinger, Isreal & Schiffmiller

[57] ABSTRACT

Benzoyoxyacetic acid derivatives of formula (I)

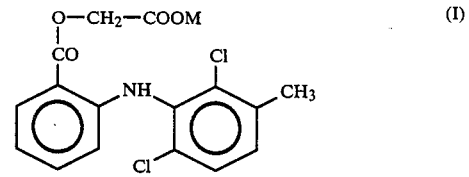

wherein M denotes hydrogen or one equivalent of a pharmaceutically acceptable inorganic or organic cation are useful as analgesics and anti-inflammatory agents. A novel process for their preparation is also disclosed along with novel intermediates.

7 Claims, No Drawings

DERIVATIVES OF BENZOYLOXYACETIC ACID, AND PREPARATION AND FORMULATIONS THEREOF FOR THERAPEUTIC USE

This invention relates to benzoyloxyacetic acid derivatives, to methods for their preparation, pharmaceutical compositions containing them and to method and intermediates useful in their production. More specifically, the invention relates to 2-[(2,6-dichloro-3-methylphenyl)-amino]benzoyloxyacetic acid and salts thereof and to pharmaceutical compositions suitable for therapeutic use containing 2-[(2,6-dichloro-3-methylphenyl)-amino]benzoyloxyacetic acid and its pharmaceutically acceptable salts.

The novel benzoyloxyacetic acid derivatives according to the invention have the following general formula (I).

<chemical structure> (I)

wherein M denotes hydrogen or one equivalent of a pharmaceutically acceptable inorganic or organic cation.

Examples of such cations include the alkali metal cations (sodium, potassium etc) and cations or zwitterions derived from basic organic compounds, e.g. amino acids containing basic groups capable of forming salts. More specific examples include the following:

a, M = H
b, M = Na
c, M = $^+NH_3-(CH_2)_n-\underset{NH_2}{CH}-COOH$ (n = 1-6)

Non-limitative examples of specific salts with amino acids containing basic groups include salts with ornithine (Ic, n=3) and lysine (Ic, n=4) etc.

Preferred salts are those which when dissolved in water at a concentration of 1M form a solution having a pH of from 5 to 9, preferably 6 to 8, most preferably 6.5 to 7.5.

Salts according to the present invention are characterised by high solubility in water and, since their solutions in water (even when unbuffered) have approximately physiological pH, they are suitable for use in preparing injectable forms and for oral, rectal and local preparations.

The invention further includes a process of producing a compound of general formula (I) as defined above, which comprises reacting a salt of 2-[(2,6-dichloro-3-methylphenyl)-amino]benzoic acid with a compound of formula HalCH₂COO(PrG)

wherein (PrG) is protecting group removable by hydrogenolysis so as to form an intermediate of formula (II)

<chemical structure> (II)

subjecting the intermediate to hydrogenolysis to remove the protecting group, whereby to form a compound of formula (I) wherein M=H, and if desired, converting the so-formed compound to a desired pharmaceutically acceptable salt.

In one method of synthesizing the compounds according to the invention, an alkali-metal salt of 2-[(2,6-dichloro-3-methylphenyl)-amino]benzoic acid (e.g. III, M=Na, K etc) is reacted with a slight excess of benzyl bromoacetate in an aprotic polar solvent <chemical structure> III <chemical structure> IV (Bz = benzyl)

The resulting benzyl ester (IV), which is itself novel, is then subjected to hydrogenolysis in solution e.g. in ethyl acetate or acetic acid. The subsequent reaction is carried out at pressures which can vary from ambient to six atmospheres, using a catalyst such as 5–10% palladium on carbon.

After the catalyst has been filtered, the organic solution is dried in vacuo and the residue (Ia) is purified by crystallization from a suitable solvent or mixture of solvents.

The acid can be converted into one of its salts (Ib-c) by treatment in aqueous alcoholic or aqueous acetone solution with the stoichiometric quantity of the desired base. The resulting salt can be isolated by crystallization or by freeze-drying the aqueous solution remaining after evaporation of the organic solvent.

The following are non-limitative examples illustrating the invention:

EXAMPLE 1

Synthesis of benzyl 2-[(2,6-dichloro-3-methylphenyl)-amino]benzoyloxyacetate (IV).

50 grams (0.16 mol) of III in the form of the sodium salt (III, M=Na-sodium meclofenamate) were dissolved in 300 ml of N,N-dimethylformamide heated to 60° C. and treated with 43.40 g (0.19 mol) of benzyl bromoacetate with agitation in a nitrogen atmosphere. The heating (60°-70° C.) and agitation were continued for 8 hours after which the reaction solvent was distilled at 70° C. in vacuo to a residual volume of 100 ml. It was diluted with 1 liter of isopropyl ether and 300 ml of water, after which the separated organic phase was washed with water, dehydrated and evaporated to dryness in vacuo. The oily residue was redissolved in isopropyl ether and precipitated by dilution with N-hexane.

54 g of a white product (76% yield) were obtained, m.p. 64° C.; $M^{(+\cdot)}$ at m/z 444; $^1$H-NMR signals (CDCl$_3$) at 9.15 ppm (s., 1H, N—H); 6.2-8.2 (m, 11H, aromatics); 5.27 (s., 2H, O—CH$_2$—Ar); 4.94 (s., 2H, O—CH$_2$—COO); 2.40 (s., 3H, CH$_3$).

Elementary analysis for C$_{23}$H$_{19}$Cl$_2$NO$_4$

|  | C | H | Cl | N |
|---|---|---|---|---|
| % Calculated | 62.16 | 4.31 | 15.96 | 3.15 |
| % Found | 62.00 | 4.36 | 15.94 | 3.14 |

EXAMPLE 2

Synthesis of 2-[(2,6-dichloro-3-methylphenyl)-amino]benzoyloxyacetic acid (Ia).

20 grams of ester IV (0.045 mol) obtained as in Example 1 were dissolved in 200 ml of ethyl acetate and, after adding 2 g of 10% palladium on carbon, were treated with hydrogen at ambient temperature and pressure. At the end of the reaction the catalyst was filtered on Celite, washing the filter with a little ethyl acetate, and the solvent was then evaporated in vacuo and the residue was recrystallized from ethyl acetate and hexane.

14.4 g (90% yield) of white product was obtained, m.p. 172°-174° C.; $M^{(+\cdot)}$ at m/z 354 and the following $^1$H-NMR (CDCl$_3$) signals at 9.15 ppm (s., 1H, N-H); 8.88 (s., 1H, COOH); 6.2-8.2 (m., 6H aromatics); 4.94 (s., 2H, O—CH$_2$—COO); 2.40 (s., 3H, CH$_3$).

Elementary analysis for C$_{16}$H$_{13}$NCl$_2$O$_4$

|  | C | H | Cl | N |
|---|---|---|---|---|
| % Calculated | 54.26 | 3.70 | 20.02 | 3.95 |
| % Found | 54.20 | 3.72 | 19.80 | 3.92 |

EXAMPLE 3

Preparation of sodium salt (Ib) of 2-[(2,6-dichloro-3-methylphenyl)-amino]benzoyloxyacetic acid by freeze-drying.

5 grams (0.014 mol) of acid (Ia) were dissolved in 150 ml of 60% aqueous acetone. The resulting mixture was cooled to 0° C. and then treated with a stoichiometric quantity of aqueous sodium bicarbonate solution. The acetone was evaporated in vacuo at 20° C. and the aqueous solution was filtered on Celite and freeze-dried.

5 g of light white product (94% yield) were obtained and had a pH of 6.9 in 1% aqueous solution.

|  | C | H | Cl | N | Na |
|---|---|---|---|---|---|
| % Calculated | 51.09 | 3.22 | 18.85 | 3.72 | 6.11 |
| % Found | 50.55 | 3.30 | 18.22 | 3.62 | 6.20 |

EXAMPLE 4

Preparation of sodium salt (Ib) of 2-[(2,6-dichloro-3-methylphenyl)-amino]benzoyloxyacetic acid by precipitation.

20 grams (0.056 mol) of acid (Ia) were dissolved in ethanol after which an alcoholic solution of sodium hydroxide (one equivalent) was added dropwise under agitation with cooling.

The resulting solution was agitated for 30 minutes under nitrogen and then evaporated to a small volume in vacuo at 30° C. The residue was taken up in isopropyl ether, giving a precipitate which was filtered in vacuo and washed with fresh solvent on the filter.

The substance was dried to 40° C. in vacuo until the weight was constant, giving 18 g of (Ib) (95% yield) in the form of a white solid, m.p. 228° C., having a pH of 7.1 in 1% aqueous solution. The salt was identical with that obtained by freeze-drying.

EXAMPLE 5

Synthesis of d,l-lysine salt (Ic) of 2-[(2,6-dichloro-3-methylphenyl)-amino]benzoyloxyacetic acid.

3.54 g (0.01 mol) of Ia was dissolved in 30 ml ethanol and a solution of 1.47 g (0.01 mol) of d,l-lysine in 10 ml water was added dropwise with cooling. The resulting solution was diluted with 50 ml ethanol and agitated at 20° C. for 2 hours. After complete precipitation of the lysine salt, the product was filtered in vacuo and washed on the filter with fresh ethanol.

The product was dried at 70° C. in vacuo until the weight was constant, giving 4.5 g of salt (90% yield) in the form of a white crystalline solid, m.p. 214°-217° C. with decomposition, having a pH of 6.75 in 1% aqueous solution.

|  | C | H | Cl | N |
|---|---|---|---|---|
| % Calculated | 52.91 | 5.41 | 8.42 | 14.20 |
| % Found | 53.00 | 5.45 | 8.30 | 14.00 |

PHARMACOLOGICAL TESTS

The anti-inflammatory and analgesic activity of compound Ib was tested after oral administration in the carrageenin oedema test in the rat (C. A. Winter et al. *Proc. Soc. Exp. Biol. Med.*, 111, 544, 1962), in the phenylquinone writhing test (I. C. Hendershot and J. J. Forsaith, *Pharmacol. Exp. Ther.*, 125, 237, 1959) and in the hot plate test on the mouse (N. B. Eddy and D. J. Leimbach, *J. Pharmacol. Exp. Ther.*, 107, 385, 1953). The activity of the compound was compared with equimolecular doses of sodium meclofenamate. A comparison was also made between the acute toxicity of the two substances by measuring the oral LD 50 on the rat.

Compound Ib had the anti-inflammatory and analgesic properties of the reference compound, both in the carrageenin oedema test and in the phenylquinone writhing test, and also showed some activity in the hot plate test whereas the reference compound remained inactive.

The comparison between the two LD 50 values is in favour of the novel derivative Ib, which was less toxic than sodium meclofenamate. This is probably also due to the difference in the pH of their aqueous solutions. Compound Ib in 1% aqueous solution has practically neutral pH whereas sodium meclofenamate has a markedly alkaline pH which is harmful to tissues. This characteristic is advantageous for injectable, rectal and local pharmaceutical forms, which are better tolerated.

Table 1 shows the results of the carrageenin oedema test on the rat. The substances under test, dissolved in distilled water, were administered by a stomach probe 1 hour before subplantar injection of carrageenin (1% in sterile 0.9% NaCl aqueous solution). The volume of the paws of the treated animals and the controls was measured by plethysmometer immediately and 1, 2, 3 and 4.5 hours after the carrageenin. Compound Ib and the reference product behaved in similar manner, antagonising the oedema to an extent depending on the dose and statistically significant at doses of 68 micromols/kg.

Table 2 shows the analgesic anti-inflammatory activity in the phenylquinone writhing test on the mouse. The substances under test were administered by a stomach probe 1 hour before intraperitoneal injection of phenylquinone (2 mg/kg). The abdominal contractions of the treated animals and the controls were counted during every 10 minutes for half an hour. In this test also, the activity of compound Ib was comparable with that of sodium meclofenamate at both the doses tried.

Table 3 shows the results of the hot plate test on the mouse. Morphine hydrochloride was used as a standard. The substances under test were administered by a stomach probe to preselected mice. The controls and the treated animals were placed on the hot plate (55° C.) one at a time immediately after treatment. The reaction time to heat, was measured 30 and 60 minutes after treatment. Animals were considered protected when the reaction time was 15 seconds or more. Compound Ib at the highest dose showed slight analgesic activity after 30 minutes.

TABLE 3

Analgesic activity of Ib in the hot plate test on the mouse. Oral administration

| Substances | Dose mg/kg | Number of Animals | Percentages of mice protected at the following times: | |
|---|---|---|---|---|
| | | | 30 minutes | 60 minutes |
| Controls | — | 10 | 0 | 0 |
| Ib | 12.7° | 10 | 0 | 0 |
| | 25.4°° | 10 | 20 | 0 |
| Sodium meclofenamate | 11° | 10 | 0 | 0 |
| | 22°° s.c. | 10 | 0 | 0 |
| Controls | — | 10 | 0 | 0 |
| Morphine HCl | 10 | 10 | 90 | 60 |

°Dose corresponding to 10 mg/kg of meclofenamic acid
°°Dose corresponding to 20 mg/kg of meclofenamic acid Table 4 shows the LD 50 of Ib and of the reference producing determined orally on male and female rats after 20 days of observation. The two LD 50 values were calculated by the probit method. Compound Ib was found to be less toxic than sodium meclofenamate, to a statistically significant extent.

TABLE 4

Acute toxicity of Ib on the rat. Oral administration

| Substances | DL50 mg/kg | Slope |
|---|---|---|
| Ib | 271 (197–422)[1] | 2.553 ± 0.6302 |

TABLE 1

Anti-inflammatory activity of Ib on carrageenin oedema in the rat. Oral administration

| Substance | Dose mg/kg | Number of Animals | Original volume (ml) m ± s.e. | Increase of original volume (m ± s.e.) | | | | |
|---|---|---|---|---|---|---|---|---|
| | | | | 1 h | 2 h | 3 h | 4 h | 5 h |
| Controls | — | 10 | 2.03 ± 0.04 | 0.47 ± 0.04 | 0.95 ± 0.10 | 1.53 ± 0.11 | 1.51 ± 0.09 | 1.55 ± 0.10 |
| Ib | 12.7° | 10 | 2.00 ± 0.06 | 0.44 ± 0.3 −6% | 0.81 ± 0.07 −15% | 1.23 ± 0.06 −20% | 1.39 ± 0.06 −8% | 1.10 ± 0.08 −10% |
| Sodium Meclofenamate | 11.0° | 10 | 2.02 ± 0.03 −13% | 0.41 ± 0.05 −8% | 0.87 ± 0.10 −7% | 1.42 ± 0.10 −6% | 1.12 ± 0.07 −10% | 1.39 ± 0.08 |
| Controls | — | 10 | 1.95 ± 0.03 | 0.45 ± 0.07 | 0.96 ± 0.08 | 1.35 ± 0.05 | 1.60 ± 0.05 | 1.65 ± 0.03 |
| Ib | 25,4°° | 10 | 2.01 ± 0.03 | 0.35 ± 0.05 −22% | 0.62 ± 0.07* −35% | 0.78 ± 0.07** −42% −31% | 1.11 ± 0.08** −26% | 1.22 ± 0.08** |
| Sodium Meclofenamate | 22,0°° | 10 | 1.98 ± 0.02 | 0.36 ± 0.05 −20% | 0.65 ± 0.05* −32% | 0.77 ± 0.07** −43% | 1.07 ± 0.09** −33% | 1.24 ± 0.07** −25% |

°Doses corresponding to 10 mg/kg of meclofenamic acid
°°Doses corresponding to 20 mg/kg of meclofenamic acid
Duncan test
*P < 0.05
**P < 0.01 vs controls
Not significant: Ib vs. sodium meclofenamate

TABLE 2

Analgesic activity of Ib on writhing induced by phenylquinone in rat. Oral administration

| Substances | Dose mg/kg | Number of Animals | 0–10 minutes | % Protection | 10–20 minutes | % Protection | 20–30 minutes | % Protection | Total 30 minutes | % Protection |
|---|---|---|---|---|---|---|---|---|---|---|
| Controls | — | 10 | 25.1 ± 1.8 | — | 20.6 ± 1.2 | — | 14.3 ± 0.9 | — | 60.0 ± 3.2 | — |
| Ib | 12.7° | 10 | 14.8 ± 2.9** | 41 | 16.6 ± 1.5 | 19 | 9.8 ± 1.0 | 31 | 41.2 ± 4.1** | 31 |
| | 25.4°° | 10 | 11.6 ± 2.5** | 54 | 12.1 ± 2.3** | 41 | 7.2 ± 1.4** | 50 | 30.9 ± 5.8** | 48 |
| Sodium meclofenamate | 11.0 | 10 | 12.0 ± 1.6** | 52 | 16.5 ± 1.0 | 20 | 8.6 ± 0.4** | 40 | 34.2 ± 1.5** | 43 |
| | 22.0 | 10 | 10.0 ± 1.1** | 60 | 13.7 ± 1.5* | 33 | 7.7 ± 0.8** | 46 | 28.0 ± 2.9** | 53 |

°Dose corresponding to 10 mg/kg of meclofenamic acid
°°Dose corresponding to 20 mg/kg of meclofenamic acid
Duncan test
*P < 0.05
**P < 0.01 vs. controls
Not significant: Ib vs. sodium meclofenamate TABLE 4-continued

| Acute toxicity of Ib on the rat. Oral administration | | |
|---|---|---|
| Substances | DL50 mg/kg | Slope |
| Sodium meclofenamate | 127 (102–152)[2] | 7.402 ± 2.014 |

1. Corresponding to 213 (155–332) mg/kg meclofenamic acid
2. Corresponding to 119 (95–142) mg/kg meclofenamic acid
PR = 1.935 (1.191–3.586)

In accordance with the pharmaco-toxicological results obtained for Ib, compounds having the general formula I have better therapeutic indications and chemical and physical characteristics which are suitable for rectal and parenteral formulations and are therefore of use in initial and maintenance treatment of inflammation and as pain-killers and against period pains.

The compounds according to the invention (I and IV) can be formulated with suitable excipients and administered, e.g. in the form of capsules, ampoules, suppositories or gels.

The anti-inflammatory activity after oral administration of compound Ib was tested in the following tests:

(1) Arachidonic acid oedema in the rat (M. J. Di Martino, G. C. Campbell Jnr., C. E. Wolff and N. Hanna, Agents and Actions; 21, 303, 1987)

Compound Ib was administered by gastric probe one hour before subplantar injection of 0.1 ml of 0.5% arachidonic acid in carbonate buffer (pH 8–8.2).

The volume of the paws of the treated animals and of the control was measured with a plethysmometer immediately and 60 minutes after the irritating agent (peak time of oedema).

The results given in Table 5 show that compound Ib is about twice as active as sodium meclofenamate used as the reference substance, the oedema being reduced in statistically significant manner at doses respectively of 1/7 and ¼ of the LD50.

TABLE 5

| Anti-Inflammatory Activity of Ib on Arachidonic Acid Oedema in the Rat Oral Administration | | | |
|---|---|---|---|
| Substance | Dose° mg/kg | Number of Animals | Increase of Original Volume (m ± s.e.) 60 min |
| Controls | — | 5 | 0.62 ± 0.03 |
| Ib | 12.7 | 5 | 0.53 ± 0.04 (−15) |
|  | 38.1 | 5 | 0.37 ± 0.05** (−40) |
| Sodium Meclofenamate | 11 | 5 | 0.58 ± 0.05 (−6) |
|  | 33 | 5 | 0.44 ± 0.06* (−29) |

°Doses corresponding to 10 and 30 mg/kg of meclofenamic acid
*P < 0.05 vs controls
**P < 0.01 vs controls (2) Irritation of 6-day old air pouch by carrageenan in the rat (A. D. Sedgwick, Y. M. Sin, A. R. Mackay, A. Al-Duaij and D. A. Willoughby; J. Pharm. Pharmacol.; 36, 171, 1984).

The formation of a dorsal pouch was induced in the rat by dorsal subcutaneous administration of 20 ml of air. 10 ml of air were then injected every day for three consecutive days in order to keep the cavity permeable. Six days after the first injection of air, the dorsal pouch in the animals was treated with 1 ml of 1% carrageenan in physiological solution.

Compound Ib was administered by gastric probe, 24 hours and 1 hour before administration of the irritating agent.

The animals, divided into groups of five, were killed 4 hours and 24 hours after the carrageenan. The volume of the exudate and the total number of leucocytes were measured.

The results, given in Table 6, show that compound Ib when tested in equimolar doses (in meclofenamic acid) was about twice as active as the reference compound in inhibiting both the volume of exudate and the total content of leucocytes.

TABLE 6

| Anti-inflammatory Activity of Ib on 6-Day Old Air Pouch of Carrageenan in the Rat. Oral Administration | | | | | | |
|---|---|---|---|---|---|---|
| | Dose mg/kg | No. of | Volume (mL) m ± s.e. | | Leucocytes (× 10[6]) m ± s.e. | |
| Substance | os | Animals | 4 h | 24 h | 4 h | 24 h |
| Controls | — | 5 | 0.32 ± 0.06 | 0.90 ± 0.06 | 4.46 ± 1.07 | 83.94 ± 6.32 |
| Ib | 31.75° × 2 | 5 | 0.24 ± 0.02 (−25) | 0.26 ± 0.06** (−71) | 1.08 ± 0.19* (−76) | 16.08 ± 6.85** (−81) |
| Sodium Meclofenamate | 27.5° × 2 | 5 | 0.30 ± 0.05 (−6) | 0.52 ± 0.12* (−42) | 4.36 ± 1.76 (−2) | 40.14 ± 11.99* (−52) |

°Doses corresponding to 25 mg/kg of meclofenamic acid
*P < 0.05 vs controls
**P < 0.01 vs controls The following examples of pharmaceutical formulations are given by way of indication and do not limit the use in treatment.

| Capsules | |
|---|---|
| Compound Ib | 106.3 mg |
| Lactose | 139.6 mg |
| Silica gel | 3.5 mg |
| Magnesium stearate | 10.0 mg |
| Sodium lauryl sulphate | 0.6 mg |
| Suppositories | |
| Compound Ic (n = 4) | 141.3 mg |
| Polyethylene glycol 1300–1700 | 2296.2 mg |
| Polyethylene glycol 380–420 | 12.5 mg |
| Polysorbate 80 | 50.0 mg |
| 2.5% gel | |
| Compound Ic (n = 4) | 3.53 g |
| Carboxypolymethylene | 1.5 g |
| Triethanolamine | 2.5 g |
| 50% lysine solution | 2.3 g |
| Polysorbate 80 | 0.8 g |
| Ethyl alcohol | 5.0 g |
| Methyl p-hydroxybenzoate | 0.1 g |
| Lavender essence | 0.1 g |
| Purified water q.s. ad | 100.0 g |
| Ampoules | |
| -Freeze-dried ampoule | |
| Compound Ic (n = 4) | 70.6 mg |
| Mannitol | 90.0 mg |
| -Solvent ampoule | |
| Water for injection | 2.5 ml |

For treating humans, a suitable daily dose is from 0.4 to 40 mg/kg, preferably 1.0 to 10 mg/kg.

For treating humans, a suitable daily dose is from 0.4 to 40 mg/kg, preferably 1.0 to 10 mg/kg.

We claim:

1. A compound having the general formula:

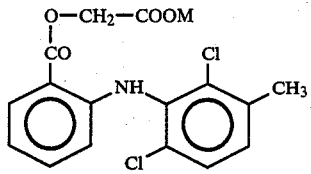 (I)

wherein M denotes hydrogen or one equivalent of a pharmaceutically acceptable inorganic or organic cation.

2. A compound according to claim 1 wherein M is a cation of an alkali metal.

3. A compound according to claim 1 wherein M is a cation or zwitterion derived from a pharmaceutically acceptable amino acid.

4. A compound according to claim 1 wherein M is:

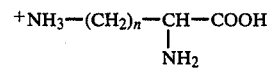

wherein n is an integer from 1 to 6.

5. A compound according to claim 4 wherein n=3 or 4.

6. A pharmaceutical composition comprising a compound according to claim 1 and a pharmaceutically acceptable excipient.

7. A method of eliciting an analgesic or anti-inflammatory response in a subject, which comprises administering an effective dose of a compound according to claim 1.

* * * * *